United States Patent [19]

Grollier et al.

[11] Patent Number: 4,504,494
[45] Date of Patent: * Mar. 12, 1985

[54] PREPARATION OF ANTHRALIN SOLUTIONS OR SUSPENSIONS IN AROMATIC ESTERS AND THEIR USE FOR DISEASES OF THE SKIN AND NAILS

[75] Inventors: Jean F. Grollier, Paris; Georges Rosenbaum, Asnieres; Josiane Allec, Pierrefitte; Braham Shroot, Antibes, all of France

[73] Assignee: Societe Anonyme dite: L'Oreal, Paris, France

[*] Notice: The portion of the term of this patent subsequent to Jan. 22, 2002 has been disclaimed.

[21] Appl. No.: 459,647

[22] Filed: Jan. 20, 1983

[30] Foreign Application Priority Data

Jan. 28, 1982 [FR] France ................ 82 01327

[51] Int. Cl.³ ............................................. A61K 31/05
[52] U.S. Cl. ............................................. 514/544; 514/568
[58] Field of Search ............................. 424/346, 365

[56] References Cited

U.S. PATENT DOCUMENTS 4,293,544 10/1981 Elmi ........................ 424/60
4,299,826 11/1981 Luedders ................... 424/181
4,326,224  1/1983 Van Scott et al. ......... 424/175

OTHER PUBLICATIONS

Remington's Pharmaceutical Sciences, 16th Ed., 1980, p. 356.
Chemical Abstracts 76:144782y, (1972).
Cosmetics, Science & Technology (Balsam et al.), 2nd Ed., vol. 1, pp. 194–195, (1972).

Primary Examiner—Leonard Schenkman
Attorney, Agent, or Firm—Wegner & Bretschneider

[57] ABSTRACT

An oxidation-stable composition is useful for the treatment of diseases of the skin and nails, which comprises a solution of dispersion of anthralin in an aromatic ester of the formula:

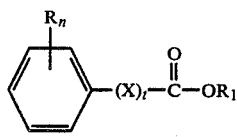

wherein
R represents H, OH, $CH_3$, or $OCH_3$,
n is 1 or 2;
$R_1$ represents a linear or branched alkyl radical having 1 to 18 carbon atoms; a cycloalkyl radical having 4 to 6 carbon atoms which is optionally substituted by an alkyl radical having 1 to 3 carbon atoms; an arylalkyl or arylalkenyl radical in which the alkyl or alkenyl radical has 1 to 3 carbon atoms; or a phenyl radical optionally substituted by an alkyl radical having 1 to 3 carbon atoms or by an alkoxy radical having 1 or 2 carbon atoms;
X represents the divalent radical $-CH_2-$, $-CH_2-CH_2-$, or $-CH=C-$; and t is 0 or 1.

7 Claims, No Drawings

PREPARATION OF ANTHRALIN SOLUTIONS OR SUSPENSIONS IN AROMATIC ESTERS AND THEIR USE FOR DISEASES OF THE SKIN AND NAILS

The present invention has as an object a composition based on anthralin or one of its derivatives and its use for the treatment of diseases of the skin and nails, particularly the treatment of acne, warts, and especially psoriasis.

Psoriasis is a particularly common dermatosis manifesting itself as lesions which are found on the elbows, the posterior surfaces of the forearms, the knees, the legs, and the sacrolumbar region, as well as on the scalp.

Among the various substances which have already been recommended for the treatment of psoriasis, particular mention should be made of anthralin or dithranol (1,8,9-trihydroxyanthracene), which has proven particularly active but which is not without some disadvantages in use, since this compound has proven particularly irritating to the parts of the skin not affected by the psoriasis and since it is very readily degraded by oxidation to dark-colored polymeric products capable of staining the skin and clothing.

It has been proposed that particularly viscous base vehicles such as vaseline, possible in association with antioxidants, be used with the object of alleviating the irritation phenomena, but it has been shown that anthralin is dispersed in vaseline and does not store well over a period of time. In addition, the elimination of vaseline-based products from the scalp and skin is very difficult, rendering their use awkward.

It has now been found that it is possible to preserve anthralin or its derivatives in excellent condition by using an aromatic ester as a vehicle.

In effect, tests involving storage over a period of time have permitted it to be shown that degradation due to the oxygen in the atmospheric air is considerably reduced, and that, in particular, the color of the composition remains constant or substantially constant. Physico-chemical determinations confirm this good stability.

In addition, it has been found that as compared to other esters, for example alkyl esters, the aromatic esters, because of their dissolving capacities, permit the production of compositions in the form of solutions with a higher concentration of anthralin or one of its derivatives.

The present invention has as an object, as a new industrial product, an anhydrous composition, stable to oxidation, based on anthralin or one of its derivatives, for the treatment of diseases of the skin and nails, particularly for psoriasis. This composition is in the form of a solution or dispersion of anthralin or one of its derivatives in an aromatic ester of the formula:

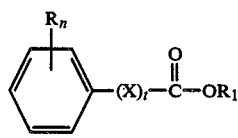

in which:

R represents H, OH, $CH_3$, or $OCH_3$ and n is 1 or 2;

$R_1$ represents a linear or branched alkyl radical having 1 to 18 carbon atoms, a cycloalkyl radical having 4 to 6 carbon atoms which may optionally be substituted by at least one alkyl radical having 1 to 3 carbon atoms, an arylalkyl or arylalkenyl radical in which the alkyl or alkenyl radical has 1 to 3 carbon atoms and the aryl is typically phenyl or ($C_{1-3}$) alkyl phenyl, a phenyl radical which may optionally be substituted by an alkyl radical having 1 to 3 carbon atoms or by an alkoxy radical having 1 or 2 carbon atoms, X represents the divalent radical $-CH_2-$, $-CH_2-CH_2-$, or $-CH=CH-$; and t is 0 or 1.

Among esters responding to formula (I) are benzyl benzoate, methyl salicylate, benzyl salicylate, ethyl o- or p-toluate, ethyl or benzyl cinnamate, isobutyl phenylacetate, benzyl phenylacetate, phenethyl phenylacetate, methyl anisate, and menthyl salicylate.

Among the anthralin derivatives which can also be stabilized by aromatic esters, mention can be made of dimeric anthralin, as well as the compounds described in French Patent Nos. 80.22454 and 80.22455.

According to the invention, the concentration of anthralin or one of its derivatives is generally between 0.01 and 5%, but preferably between 0.05 and 2.5%.

The composition according to the invention as defined above can be used as is in the local treatment of diseases of the skin, the scalp, and the nails, particularly for psoriasis, but is preferably used in a form thickened, for example, with the aid of a thickener which does not modify the stability and is chosen from among compounds such as silicas, polyethylene powders, and nylon powders.

The following silicas can be mentioned:

"Aerosil R. 912" (hydrophobic silica) sold by DEGUSSA;

"Aerosil 200" silica sold by DEGUSSA;

"HDK N 20 E" (pyrogenic silica) sold by WACKER.

Very particular mention can be made of the polyethylene powder sold under the name "Polyethylene AC 6 A" by ALLIED CHEMICAL.

The use of relatively thick compositions has the advantage of preventing any risk of flowing and thus preventing irritation phenomena on the healthy parts of the skin.

Other ingredients, for example salicylic acid and/or an antioxidant, can be introduced into the composition.

The compositions of this invention can also be mixed at the moment of use with a cosmetic base, for example a shampoo or any other cosmetic formulation intended for the treatment of the skin or scalp. These compositions are preferably applied at an acid pH. In this case, the compositions are made available in the form of a two-part package, the first part consisting of the composition based on anthralin or one of its derivatives and the other part consisting of the cosmetic base.

As an illustration, several non-limiting examples of compositions according to this invention based on anthralin or one of its derivatives will now be given.

EXAMPLE I

Pre-shampoo composition.
Anthralin: 1.6 g
Salicylic acid: 0.1 g
Benzyl salicylate to make: 100 g

EXAMPLE II

Pre-shampoo composition.
Anthralin: 0.5 g

Benzyl salicylate to make: 100 g

EXAMPLE III

Shampoo

One part composition (1) below is mixed as needed with seven parts composition (2) below:
Composition (1)
Anthralin: 0.8 g
Benzyl salicylate to make: 100 g
Composition (2)
Nonionic surfactant of the formula:

R—CHOH—CH$_2$O—(CH$_2$—CHOH—CH$_2$O)$_n$H

R=C$_9$—C$_{12}$alkyl, n=3,5: 17 g
Formaldehyde: 0.06 g
Citric acid to pH=3
Benzyl benzoate to make: 100 g

EXAMPLE IV

Composition for the skin.
Anthralin: 0.5 g
HDK n 20 E silica: 8 g
Benzyl benzoate to make: 100 g

EXAMPLE V

Pre-shampoo composition.
Anthralin: 1.2 g
Ethyl o-toluate to make: 100 g

EXAMPLE VI

Shampoo

One part composition (1) below is mixed as needed with 6 parts composition 2 below:
Composition (1)
Anthralin: 1 g
Methyl salicylate to make: 100 g
Composition (2)
Nonioic surfactant of the formula

R—CHOH—CH$_2$O—(CH$_2$—CHOH—CH$_2$O)$_n$H

R=C$_9$—C$_{12}$ alkyl, n=3.5: 15 g
Ammonium laurylsulfate: 4 g
Citric acid to pH=3
Water to make: 100 g

EXAMPLE VII

Composition for the skin.
Anthralin: 0.5 g
AC 6 A polyethylene (sold by ALLIED CHEMICAL): 7.5 g
Isobutyl phenylacetate to make: 100 g

EXAMPLE VIII

Composition for the skin.
Anthralin: 2.3 g
Ethyl cinnamate to make: 100 g

EXAMPLE IX

Composition for the scalp (pre-shampoo) or the skin.
Anthralin: 0.8 g
Benzyl benzoate to make: 100 g

EXAMPLE X

Composition for the scalp (pre-shampoo) or the skin.
Anthralin: 1.5 g
HDK n 20 E silica: 5 g
Ethyl p-toluate to make: 100 g

EXAMPLE XI

Composition for the scalp (pre-shampoo) or the skin.
Anthralin: 1.3 g
HDK n 10 E silica: 5.2 g
Ethyl cinnamate to make: 100 g

EXAMPLE XII

Composition for the scalp (pre-shampoo) or the skin.
Anthralin: 2.5 g
Ethyl p-toluate to make: 100 g

EXAMPLE XIII

Composition for the skin.
Anthralin: 0.8 g
HDK n 20 E silica: 4.5 g
Benzyl benzoate to make: 100 g

EXAMPLE XIV

Composition for the skin.
Anthralin: 0.5 g
HDK n 20 E silica: 5.3 g
Ethyl cinnamate to make: 100 g

EXAMPLE XV

Pre-shampoo composition for the scalp (prepared under an inert atmosphere at a temperature higher than the melting point of benzyl cinnamate).
Anthralin: 0.7 g
Benzyl cinnamate to make: 100 g

EXAMPLE XVI

Shampoo

One part composition (1) below is mixed as needed with 7 parts composition (2) below:
Composition (1) (prepared under an inert atmosphere)
Anthralin: 2.8 g
Methyl anisate: 100 g
Composition (2)
Nonionic surfactant of the formula:

R—CHOH—CH$_2$O—(CH$_2$—CHOH—CH$_2$O)$_n$H

R=C$_9$-C$_{12}$ alkyl, n=3.5 17 g
Formaldehyde: 0.06 g
Citric acid to pH 3
Water to make: 100 g

EXAMPLE XVII

Composition for the scalp (pre-shampoo) or the skin (prepared under an inert atmosphere).
Anthralin: 1.5 g
Methyl anisate to make: 100 g

EXAMPLE XVIII

Composition for the scalp (pre-shampoo) or the skin.
Anthralin: 1.5 g
HDK n 10 E silica: 6 g
Phenethyl phenylacetate to make: 100 g

EXAMPLE XIX

Composition for the scalp (pre-shampoo) or the skin.
Anthralin: 0.3 g
HDK n 20 E silica: 6 g Menthyl salicylate to make: 100 g

EXAMPLE XX

Composition for the scalp (pre-shampoo) or the skin.
Anthralin: 1.6 g
HDK n 20 E silica: 6 g
Benzyl phenylacetate to make: 100 g When applied to parts of the skin or scalp in an amount sufficient to cover the lesions, compositions of Examples I-XX above make it possible, after a treatment period of 3 to 5 weeks, to effect a regression and cure of the skin diseases, in particular psoriasis.

We claim:

1. An oxidation stable composition for the treatment of skin diseases, comprising a solution or dispersion containing 0.01 to 5% by weight of anthralin in an aromatic ester of the formula:

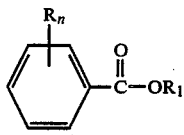

wherein
R represents H, OH, $CH_3$, or $OCH_3$,
n is 1 or 2; and
$R_1$ represents phenyl, ($C_1$-$C_3$) alkyl phenyl, or benzyl.

2. A composition according to claim 1 wherein the anthralin is present in a concentration of 0.05 to 2.5%.

3. A composition according to claim 1 wherein the aromatic ester is selected from the group consisting of benzyl benzoate and benzyl salicylate.

4. A composition according to claim 1 wherein the composition additionally contains a thickener selected from the group consisting of silica, polyethylene powder and nylon powder.

5. A process for the treatment of skin diseases which comprises topically applying to the lesions to be treated an effective amount of a composition according to claim 1.

6. The process of claim 5 wherein the disease to be treated is psoriasis.

7. The process of claim 5 wherein the composition containing anthralin constitutes the active ingredient of the first part of a two-part package, the second part being a cosmetic base and the two parts being mixed at the moment of use.

* * * * *